(12) United States Patent
Frye et al.

(10) Patent No.: US 10,934,605 B2
(45) Date of Patent: Mar. 2, 2021

(54) METHODS FOR SYNTHESIZING HIGH PURITY NIOBIUM OR RHENIUM POWDERS

(71) Applicant: Battelle Memorial Institute, Richland, WA (US)

(72) Inventors: John G. Frye, Richland, WA (US); Kenneth Scott Weil, Richland, WA (US); Curt A. Lavender, Richland, WA (US); Jin Yong Kim, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 606 days.

(21) Appl. No.: 15/786,289

(22) Filed: Oct. 17, 2017

(65) Prior Publication Data

US 2018/0037975 A1 Feb. 8, 2018

Related U.S. Application Data

(63) Continuation of application No. 12/700,923, filed on Feb. 5, 2010, now Pat. No. 9,802,834.

(51) Int. Cl.
*B22F 9/24* (2006.01)
*C22C 27/00* (2006.01)
(Continued)

(52) U.S. Cl.
CPC ............ *C22B 34/24* (2013.01); *B22F 1/0044* (2013.01); *B22F 9/24* (2013.01); *C01G 33/00* (2013.01);
(Continued)

(58) Field of Classification Search
CPC ........ C01G 1/02; C01G 47/00; C01G 47/003; C01G 47/006; C22C 1/045; C22C 1/058; C22C 1/1026; C22C 27/00; C22C 27/02; C22C 27/04; C22C 29/12; C22C 32/0005; C22C 32/001; C22C 32/0015; C22C 32/0031; B01J 6/008; B01J 23/16; B01J 23/32; B01J 23/36; B01J 23/64;
(Continued)

(56) References Cited

U.S. PATENT DOCUMENTS 2,935,399 A * 5/1960 Campbell ............... C22B 61/00
75/365
3,330,697 A 7/1967 Pechini
(Continued)

OTHER PUBLICATIONS

J. J. Kingsley, K. Suresh, K. C. Patil, "Combustion synthesis of fine-particle metal aluminates," Journal of Materials Science, 25, 1990, pp. 1305-1312. (Year: 1990).*
(Continued)

*Primary Examiner* — Vanessa T. Luk
(74) *Attorney, Agent, or Firm* — Wells St. John P.S.

(57) ABSTRACT

Methods are provided for synthesizing high purity niobium or rhenium powders by a combustion reaction. The methods can include: forming a combustion synthesis solution by dissolving in water an oxidizer, a fuel, and at least one base-soluble, ammonium salt of niobium or rhenium in amounts that yield a stoichiometric burn when combusted; and heating the combustion synthesis solution to a temperature sufficient to substantially remove the water and to initiate a self-sustaining combustion reaction.

8 Claims, 1 Drawing Sheet

(51) Int. Cl.
| | |
|---|---|
| *C22B 34/24* | (2006.01) |
| *B22F 1/00* | (2006.01) |
| *C01G 33/00* | (2006.01) |
| *C01G 41/02* | (2006.01) |
| *C01G 47/00* | (2006.01) |
| *C22C 1/04* | (2006.01) |
| *C22C 1/05* | (2006.01) |
| *C22C 27/04* | (2006.01) |
| *C01G 39/02* | (2006.01) |
| *C22C 27/02* | (2006.01) |
| *C01B 21/38* | (2006.01) |
| *C07C 229/06* | (2006.01) |
| *G01N 23/20* | (2018.01) |

(52) U.S. Cl.
CPC ............ *C01G 39/02* (2013.01); *C01G 41/02* (2013.01); *C01G 47/00* (2013.01); *C22C 1/045* (2013.01); *C22C 1/058* (2013.01); *C22C 27/00* (2013.01); *C22C 27/02* (2013.01); *C22C 27/04* (2013.01); *B22F 2301/20* (2013.01); *C01B 21/38* (2013.01); *C07C 229/06* (2013.01); *G01N 23/20075* (2013.01)

(58) Field of Classification Search
CPC ...... B01J 23/656; B01J 23/6567; B01J 23/68; B01J 23/688; B01J 23/84; B01J 23/889; B01J 23/8896; B01J 23/8986; B01J 27/186; B01J 27/187; B01J 29/0341; B01J 29/0358; B01J 29/045; B01J 29/076; B01J 29/16; B01J 29/26; B01J 29/48; B01J 29/58; B01J 29/64; B01J 29/69; B01J 29/78; B01J 31/32; B01J 2523/74; B01J 2531/74; C04B 35/62818; C04B 35/62855; C04B 41/5133; C04B 2111/00431; C04B 2235/3231; C04B 2235/3262; C04B 2235/3268; C04B 2235/404; C04B 2237/404; C22B 34/00; B22F 9/16; B22F 9/18; B22F 9/20; B22F 9/22; B22F 9/24; B22F 9/26; B22F 9/28; B22F 9/30; B22F 9/305; B22F 2009/165; B22F 2009/245; B22F 2201/01; B22F 2201/013; B22F 2201/016; B22F 2301/20; B22F 2302/25
See application file for complete search history.

(56) References Cited

U.S. PATENT DOCUMENTS

| | | | |
|---|---|---|---|
| 5,061,682 A | 10/1991 | Aksay et al. | |
| 5,114,702 A | 5/1992 | Pederson et al. | |
| 5,468,427 A | 11/1995 | Stangle et al. | |
| 5,984,997 A | 11/1999 | Bickmore et al. | |
| 6,171,571 B1 | 1/2001 | Bedard et al. | |
| 6,183,716 B1 | 2/2001 | Sleight et al. | |
| 6,319,421 B1* | 11/2001 | Yun .................. | B82Y 30/00 252/62.9 PZ |
| 6,835,367 B2 | 12/2004 | James et al. | |
| 7,022,155 B2 | 4/2006 | Deegan et al. | |
| 7,032,800 B2 | 4/2006 | Subramanian et al. | |
| 7,337,940 B2 | 3/2008 | Subramanian et al. | |
| 7,449,128 B2 | 11/2008 | Krishna et al. | |
| 8,361,178 B2 | 1/2013 | Liu et al. | |
| 2003/0097903 A1* | 5/2003 | Deegan .............. | B01J 19/088 75/10.21 |
| 2005/0025700 A1 | 2/2005 | Bulian et al. | |
| 2005/0129565 A1 | 6/2005 | Ohriner et al. | |
| 2005/0211018 A1 | 9/2005 | Jurewicz et al. | |
| 2006/0182677 A1* | 8/2006 | Myeong ............ | C01G 49/0036 423/263 |
| 2008/0223175 A1 | 9/2008 | Lunk et al. | |
| 2008/0246004 A1* | 10/2008 | Krishna ............ | C09K 11/7769 252/301.4 R |
| 2010/0136369 A1 | 6/2010 | Ayer et al. | |
| 2010/0279146 A1 | 11/2010 | Rowe et al. | |
| 2011/0194970 A1 | 8/2011 | Frye et al. | |

OTHER PUBLICATIONS

A.S. Mukasyan and P. Dinka, "Novel Approached to Solution-Combustion Synthesis of Nanomaterials," International Journal of Self-Propagating High-Temperature Synthesis, vol. 16, No. 1, pp. 23-35, 2007.

Mukasyan et al., "Solution combustion synthesis of nanomaterials," Proceedings of the Combustion Institute, 31 (2007), pp. 1789-1795.

Naik, Mallari A; Mishra, Braja Gopal; Dubey, Amit, "Combustion synthesized WO3—ZrO2 nanocomposites as catalyst for the solvent-free synthesis of courmarins," Colloids and Surfaces A: Physiochem. Eng. Aspects, 317 (2008) pp. 234-238.

S. Sasikumar and R. Vijayaraghavan, "Solution combustion synthesis of bioceramic calcium phosphates by single and mixed fuels—A comparative study," Ceramics International, 34, pp. 1373-1379, available online Apr. 10, 2007.

Sergi L. Gonzales-Cortes, et al, "Rationalizing the catalytic performance of y-alumina-supported Co(Ni)—Mo(W) HDS catalysts prepared by urea-matrix combustion synthesis," Catalysis Letters, vol. 111, Nos. 1-2, pp. 57-66, Oct. 2006.

* cited by examiner

METHODS FOR SYNTHESIZING HIGH PURITY NIOBIUM OR RHENIUM POWDERS

This patent is a continuation of U.S. patent application Ser. No. 12/700,923 which was filed on Feb. 5, 2010, entitled "Production of Nanocrystalline Metal Powders via Combustion Reaction Synthesis", the entirety of which is incorporated by reference herein.

STATEMENT REGARDING FEDERALLY SPONSORED RESEARCH OR DEVELOPMENT

This invention was made with Government support under Contract DE-AC0576RL01830 awarded by the U.S. Department of Energy. The Government has certain rights in the invention.

BACKGROUND

Tungsten, molybdenum, rhenium, and niobium, as well as alloys based on each, can exhibit the mechanical properties desired for applications requiring high hardness, optimized compressive strength, and good ductility. Exemplary applications can include, but are not limited to, incandescent light filaments, welding tips, and friction stir welding tools. However, synthesis of powders of these materials exhibiting the appropriate composition and microstructure, is relatively costly and difficult to scale-up. In particular, powders having nano-sized crystallites can be especially challenging to produce on a large scale. Accordingly, a need exists for methods of synthesizing nanocrystalline metal powders of tungsten, molybdenum, rhenium, niobium, or their alloys and for nanocrystalline metal powders having the appropriate mechanical properties.

SUMMARY

Methods are provided for synthesizing high purity niobium powders by a combustion reaction. The methods can include: forming a combustion synthesis solution by dissolving in water an oxidizer, a fuel, and at least one base-soluble, ammonium salt of niobium in amounts that yield a stoichiometric burn when combusted; and heating the combustion synthesis solution to a temperature sufficient to substantially remove the water and to initiate a self-sustaining combustion reaction. Methods are also provided for synthesizing high purity rhenium powders by a combustion reaction. These methods can include: forming a combustion synthesis solution by dissolving in water an oxidizer, a fuel, and at least one base-soluble, ammonium salt of rhenium in amounts that yield a stoichiometric burn when combusted; and heating the combustion synthesis solution to a temperature sufficient to substantially remove the water and to initiate a self-sustaining combustion reaction.

As used herein, nanograin can refer to crystallographically distinguishable regions, which typically comprise regular arrays of atoms separated by boundaries of less crystalline order, within a porous or non-porous polycrystalline body or a powder particle on the order of 500 nm or smaller in size. Typically the term "nanograin" is used to describe the microstructure of a final densified body made from nanocrystalline metal powders via a powder metallurgy process (e.g. powder pressing and sintering). "Nanocrystalline" can refer to the microstructure of a porous or non-porous polycrystalline body or powder particle that comprises an aggregate of nanograins (i.e., crystallographically distinguishable regions that are on the order of 500 nm or smaller in size). As used herein, the term "nanocrystalline" is typically reserved to describe the microstructures of the powder particles that are fabricated at various stages of the present invention. For example, while an individual powder particle may be one micron in size, it may be an aggregate of crystallites that are less than 100 nm in size. Accordingly, a particle, as used herein, can refer to the individual pieces or granules that make up a powder mass. As discussed above, each powder particle may in turn be composed of a group of crystallites that are physically or chemically bound together. Alternatively an individual powder particle may be composed of a single crystallite (i.e. a single crystal or single crystallographically distinguishable regular array of atoms).

Methods for synthesizing the nanocrystalline metal powders by a combustion reaction are characterized by forming a combustion synthesis solution by dissolving in water an oxidizer, a fuel, and a base-soluble, ammonium precursor of tungsten molybdenum, rhenium, or niobium in amounts that yield a stoichiometric burn when combusted. The combustion synthesis solution is then heated to a temperature sufficient to substantially remove water and to initiate a self-sustaining combustion reaction. Exemplary base-soluble ammonium precursors of tungsten, molybdenum, rhenium, and niobium include, but are not limited to, ammonium metatungstate, ammonium heptamolybdate, ammonium niobate(v) oxalate hydrate, and ammonium perrhenate, respectively.

In some embodiments, alloys of tungsten, molybdenum, rhenium, and/or niobium can be prepared by dissolving a plurality of base-soluble, ammonium precursors in the combustion synthesis solution. Alternatively, or in addition, a nitrate precursor of an alloying metal can be dissolved in the combustion synthesis solution. Exemplary alloying metals can include, but are not limited to, transition metals that form alloy systems readily reduced from their oxides in hydrogen, such as copper, nickel, iron, cobalt, and manganese.

Exemplary oxidizers include, but are not limited to, nitric acid, metal salts (such as nitrates and sulfates), and ammonium nitrate. In some instances, the nitrate precursor can serve as an oxidizer, minimizing, or eliminating the need for addition of a separate oxidizer. The fuel comprises a reducing agent, including but not limited to sugars, amines, keggin-structured metal salts, glycine, and/or a complexing agent.

Products of the combustion reaction comprise tungsten oxide, molybdenum oxide, rhenium oxide, or niobium oxide and are characterized by powder particles having crystallites averaging less than 60 nm in size. In preferred embodiments, the nanocrystallites are less than 60 nm in size.

In another embodiment, a product of the combustion reaction is heated for less than six hours in a reducing atmosphere at a temperature less than 850° C. Reduction of the combustion reaction product can result in a non-oxidized powder. Exemplary reducing atmospheres based on hydrogen can include as much as 100% $H_2$ to as little as 2.75% $H_2$ mixed with an inert gas (e.g., nitrogen, argon, helium, etc.). Alternative reducing atmospheres can be utilized while still falling within the scope and spirit of the present invention.

After reduction, the nanocrystalline metal powder can comprise elemental or alloyed tungsten, molybdenum, rhenium or niobium and is characterized by flowable agglomerated particles consisting of crystallites averaging less than 200 nm in size. Typically, the crystallites average 30-60 nm in size. In preferred embodiments, the crystallites are less than 60 nm in size.

In another embodiment, after reduction, the surfaces of the nanocrystalline metal powder particles can be passivated with a very thin oxide layer. Passivation can occur by cooling the powder to a temperature below 100° C. and then introducing a mildly oxidizing gas. Exemplary gases can include, but are not limited to, carbon dioxide, oxygen diluted in an inert gas, water vapor, or combinations thereof.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions, the various embodiments, including the preferred embodiments, have been shown and described. Included herein is a description of the best mode contemplated for carrying out the invention. As will be realized, the invention is capable of modification in various respects without departing from the invention. Accordingly, the drawings and description of the preferred embodiments set forth hereafter are to be regarded as illustrative in nature, and not as restrictive.

DESCRIPTION OF DRAWINGS

Embodiments of the invention are described below with reference to the following accompanying drawings.

DETAILED DESCRIPTION

Figure 1:
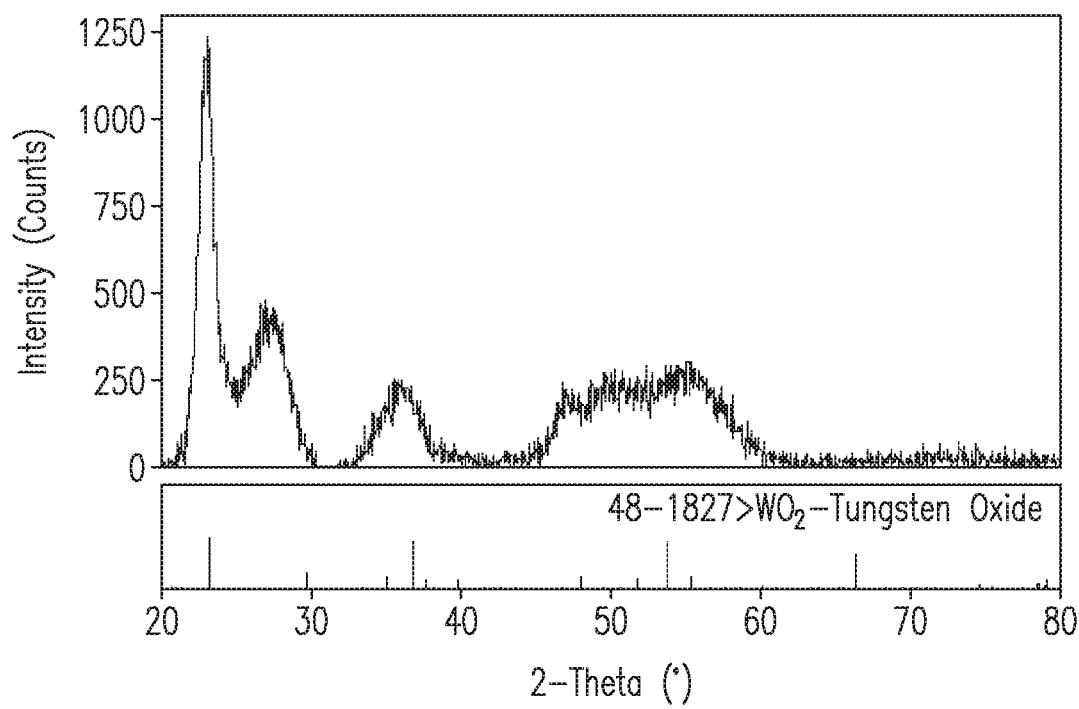
FIG. 1 is an X-ray diffraction pattern for a tungsten oxide powder, which was formed according to embodiments of the present invention, prior to reduction.

The following description includes the preferred best mode of one embodiment of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Embodiments of the present invention involve both the formation of an aqueous solution containing the appropriate precursors as well as the heating of the combustion synthesis solution to dryness and eventual autoignition. Once the precursor is ignited, a self-sustaining combustion reaction produces a final powder comprising an oxide comprising tungsten, molybdenum, rhenium, and/or niobium. According to the present invention, the resulting powder can exhibit a nanocrystalline nature and a high degree of phase homogeneity.

Example: Nanocrystalline Tungsten Powder Synthesis

In the instant example, a tungsten oxide powder, which can be reduced to yield a nanocrystalline tungsten powder, is synthesized. For 100 g of tungsten metal powder, 138.2 g of Ammonium Metatungstate (AMT; $(NH_4)_6H_2W_{12}O_{40} \cdot 5H_2O$, F.W.=3048.1 g/mole, % W by weight=72.3%) is required as a tungsten source. Additional combustion synthesis solution materials include nitric acid and glycine. In order to produce the necessary stoichiometric burn when combusted, equal amounts of oxidizing and reducing capacity must be present in the combustion synthesis solution. Additional details regarding the determination of oxidizing and reducing capacities of various materials is provided by J. J. Kingsley and L. R. Pedersen in "Energetic Materials in Ceramic Synthesis" (Mat. Res. Soc. Symp. Proc. 296 (1993) 361-366), which details are incorporated herein by reference. Briefly, the molecular formulas of each of the reagents are determined to be either net oxidizing agents or net reducing agents on a per mole basis. The relative molar ratios of the reagents required for a stoichiometric burn can then be calculated. The oxidizing and reducing capacities for the reagents of the present example are determined as follows.

For $AMT = (NH_4)_6H_2W_{12}O_{40}$ $N = 6 \cdot 0 = 0$ $H = 26 \cdot -1 = -26$ $O = 40 \cdot +2 = +80$ $\underline{W = 12 \cdot -6 = -72}$ Sum = −18 per mole (net reducing)

For Nitric Acid = $HNO_3$ $H = 1 \cdot -1 = -1$ $N = 1 \cdot 0 = 0$ $\underline{O = 3 \cdot +2 = +6}$ Sum = +5 per mole (net oxidizing)

For Glycine = $NH_2CH_2COOH$ $C = 2 \cdot -4 = -8$ $H = 5 \cdot -1 = -5$ $N = 1 \cdot 0 = 0$ $\underline{O = 2 \cdot +2 = +4}$ Sum = −9 per mole (net reducing)

In the particular instance, it was desired to keep the AMT to glycine molar ratio at 1 to 6. Therefore, the molar ratio of nitric acid to AMT necessary for a stoichiometric burn ratio can be determined as follows.

$1 \cdot AMT(@-18 \text{ per mole}) = -18$ (net reducing)

$6 \cdot Glycine(@-9 \text{ per mole}) = -54$ (net reducing)

Sum = −72 (net reducing)

For a stoichiometric burn ratio, net reducing capacity must be equal to net oxidizing capacity, so the sum of the net oxidizing capacity of the nitric acid needs to be +72.

+72÷+5 per mole of Nitric Acid=14.4 mole of $HNO_3$ per mole of AMT

In view of the above, the molar ratio of the three reactants required for a stoichiometric burn ratio are as follows.

AMT:Glycine:$HNO_3$=1:6:14.4

The amount of water to produce a satisfactory combustion synthesis solution has preferably been found to be ~20 g of D.I. water per 50 g of AMT to be used in the procedure. Generally as little water is used as possible in order to produce a stable solution containing the appropriate amounts of the reagent materials. The recipe for preparing the combustion synthesis solution of the present example is determined as follows:

1) 138.1597 g of AMT (0.045327 mole of AMT)
2) (138.1597 g÷50 g)·20 g $H_2O$=55.26 g of D.I. water needed
3) 14.4·(0.045327 mole)=0.652709 mole of $HNO_3$·63.01 g $HNO_3$ per mole·0.700=58.7531 g of 70% $HNO_3$ solution needed
4) 6·(0.045327 mole)=0.271962 mole of glycine·75.07 g glycine per mole=20.4162 g glycine needed The combustion synthesis solution was prepared in a 500 ml Erlenmeyer flask with a tight fitting screw cap. The AMT was weighed out and transferred to the clean, dry Erlenmeyer flask. D.I. water was then added to the AMT solid in the flask, which was capped and gently shaken periodically until all of the AMT solid had dissolved. The 70% nitric acid solution was slowly added to the flask with periodic shaking. Near the end of the nitric acid addition, a white solid precipitated from the solution. Glycine was then weighed out and also added to the flask. After adding the glycine, the mixture was vigorously shaken to mix the contents. After several minutes the previously precipitated solid had redissolved resulting in a yellow colored solution that was slightly turbid.

The combustion synthesis solution decomposition, or burn, was carried out using a 4 L stainless steel beaker heated on a hotplate to near red heat temperature. After the hotplate has heated the beaker bottom to near red heat, the entire combustion synthesis solution is quickly poured into the hot beaker, then the beaker covered with a clean 100 mesh sieve to contain most of the solid particles produced, while allowing steam and combustion gasses to escape from the beaker. Steam is rapidly evolved for ~5 minutes, then red colored $NO_x$ fumes are evolved as the combustion process begins to initiate. When the $NO_x$ evolution subsides, the beaker containing the porous ash is removed from the hotplate and allowed to cool to room temperature. The entire burn process was completed within less than 10 minutes. After cooling, the dark brown colored ash was recovered from the beaker, and ground to a fine powder (almost gray in color). The finely divided powder was then ready to be reduced to metallic tungsten powder.

Example: 80 at % W-20 at % Nb

In the instant example, an 80 atom % W-20 atom % Nb powder is synthesized that can yield approximately 10 g of a nanocrystalline W-Nb metal powder after reduction. Standard grade AMT was used as the source of tungsten. Ammonium Niobate(V) Oxalate hydrate (ANO; $(NH_4)Nb(O)(C_2O_4)_2 \cdot xH_2O$; F.W.=302.984 g/mole; % Nb by Wt.=20.25%) was used as the source of Nb. Ethanolamine {$(NH_2)CH_2CH_2OH$; F.W.=61.09 g/mole}, 70% nitric acid, and deionized water were also included to form the combustion synthesis solution.

Using the same methodology as described elsewhere herein, the molar ratio of the reactants to produce a stoichiometric burn is as follows.

AMT:ANO:$HNO_3$:Ethanolamine=1:3.00:18.6:4.154

Accordingly, the amounts for preparing the combustion synthesis solution is as follows.

1) 12.2663 g of AMT (0.004024 mole of AMT)
2) ~20 g of D.I. water was used in this procedure
3) 5.5390 g of ANO (0.012073 mole ANO)
4) 18.6·(0.004024 mole)=0.074846 mole of $HNO_3$·63.01 g $HNO_3$ per mole·0.700=6.7372 g of 70% $HNO_3$ solution needed
5) 4.154·(0.004024 mole)=0.016716 mole of ethanolamine·61.09 g ethanolamine per mole=1.0212 g ethanolamine needed The combustion synthesis solution can be prepared in two steps. A first solution containing the above amount of ethanolamine, half of the above amount of the water, and the above amount of the 70% nitric acid solution was prepared then set aside. A second solution containing the above amount of the ANO and half of the above amount of water was first heated gently to dissolve the ANO solid, then the above amount of AMT was added and again gently heated until all of the solids were dissolved. The two solutions were then mixed together to obtain the final combustion synthesis solution.

The combustion synthesis solution is burned in a 600 ml stainless steel beaker, which is heated on a hotplate to near red heat temperature. After the hotplate has heated the beaker bottom to near red heat, the entire combustion synthesis solution is quickly poured into the hot beaker, then the beaker covered with a clean 100 mesh sieve to contain most of the solid particles produced, while allowing steam and combustion gasses to escape from the beaker. Steam is rapidly evolved for ~5 minutes, then red colored $NO_x$ fumes are evolved as the combustion process begins to initiate. When the $NO_x$ evolution subsides, the beaker containing the porous ash is removed from the hotplate and allowed to cool to room temperature. Typically, the entire burn process can be completed within less than 10 minutes. After cooling, the ash is recovered from the beaker, and ground to a fine powder. 12.86 g of the finely divided powder was recovered and was ready to be reduced.

Example: 95 at % W-5 at % Mo

In the instant example, a 95 atom % (97.33 wt %)W-5 atom % (2.67 wt %)Mo powder is synthesized that can yield ~50 g of a nano-particulate W—Mo metal powder. Standard grade AMT was used as the source of W for this procedure. Ammonium Heptamolybdate tetrahydrate (AHM) was used as the source of Mo. Ethanolamine, 70% nitric acid, and deionized water were also included to form the combustion synthesis solution. Using the same methodology as described elsewhere herein, the molar ratio of the reactants required to produce a stoichiometric burn is as follows.

$$AMT:AHM:HNO_3:Ethanolamine=1:0.09:14.724:4.154$$

The amounts for preparing the combustion synthesis solution was determined as follows:
1) 67.2355 g of AMT (0.022058 mole of AMT)
2) ~100 g of D.I. water was used in this procedure
3) 2.4578 g of AHM (0.001989 mole AHM)
4) 14.724·(0.022058 mole)=0.324782 mole of $HNO_3$·63.01 g $HNO_3$ per mole·0.700=29.2342 g of 70% $HNO_3$ solution needed
5) 4.154·(0.022058 mole)=0.091629 mole of ethanolamine·61.09 g ethanolamine per mole=5.5975 g ethanolamine needed The combustion synthesis solution for this preparation can be done in two steps. A first solution containing the above amount of ethanolamine, half of the above amount of the water, and the above amount of the 70% nitric acid solution was prepared then set aside. A second solution was prepared containing the above amount of the AMT, half of the above amount of water, and the above amount of the AHM. The two solutions were then mixed together to obtain the final combustion synthesis solution.

The combustion synthesis solution burn is carried out using a 4 L stainless steel beaker, which is heated on a hotplate to near red heat temperature. After the hotplate has heated the beaker bottom to near red heat, the entire combustion synthesis solution is quickly poured into the hot beaker, then the beaker covered with a clean 100 mesh sieve to contain most of the solid particles produced, while allowing steam and combustion gasses to escape from the beaker. Steam is rapidly evolved for ~2-3 minutes, then red colored $NO_x$ fumes are evolved as the combustion process begins to initiate. When the $NO_x$ evolution subsides, the beaker containing the porous ash is removed from the hotplate and allowed to cool to room temperature. Typically, the entire burn process can be completed within less than 5 minutes. After cooling, the ash is recovered from the beaker, and ground to a fine powder. 64.78 g of the finely divided powder was recovered and can be reduced.

Example: 96 at % W-4 at % Re (95.95 wt % W-4.05 wt % Re)

In the instant example, a 96 atom % W-4 atom % Re (95.95 wt % W-4.05 wt % Re) powder is synthesized that can yield ~50 g of a nano-particulate W—Re metal powder after reduction. Standard grade AMT was used as the source of W and Ammonium Perrhenate (APR; $NH_4ReO_4$; F.W.=268.24 g/mole; Assay: % Re by Wt.=69.4%) was used as the source of Re for this procedure. Ethanolamine, 70% Nitric Acid Solution, and deionized water were also included to form the combustion synthesis solution.

Using the same methodology as described elsewhere herein, the molar ratio of the reactants required to produce a stoichiometric burn is as follows.

$$AMT:APR:HNO_3:Ethanolamine=1:0.5:14.7:4.154$$

The amounts for preparing the combustion synthesis solution are as follows.
1) 66.2825 g of AMT (0.021746 mole of AMT)
2) ~100 g of D.I. water was used in this procedure
3) 2.9300 g of APR (0.010921 mole APR)
4) 14.7·(0.021746 mole)=0.319666 mole of $HNO_3$·63.01 g $HNO_3$ per mole·0.700=28.7730 g of 70% $HNO_3$ solution needed
5) 4.154·(0.021746 mole)=0.090326 mole of ethanolamine·61.09 g ethanolamine per mole=5.5180 g ethanolamine needed The combustion synthesis solution for this preparation can be done in two steps. A first solution containing the above amount of ethanolamine, half of the above amount of the water, and the above amount of the 70% nitric acid solution was prepared then set aside. A second solution containing the above amount of the AMT, half of the above amount of water, and the above amount of the APR was gently heated to dissolve the solids. The two solutions were then mixed together to obtain the final combustion synthesis solution.

The combustion synthesis solution burn is carried out using a 4 L stainless steel beaker, which is heated on a hotplate to near red heat temperature. After the hotplate has heated the beaker bottom to near red heat, the entire combustion synthesis solution is quickly poured into the hot beaker, then the beaker is covered with a clean 100 mesh sieve to contain most of the solid particles produced, while allowing steam and combustion gasses to escape from the beaker. Steam is rapidly evolved for ~7-8 minutes, then red colored $NO_x$ fumes are evolved as the combustion process begins to initiate. When the $NO_x$ evolution subsides, the beaker containing the porous ash is removed from the hotplate and allowed to cool to room temperature. Typically, the entire burn process can be completed within less than 10 minutes. After cooling, the ash is recovered from the beaker, and ground to a fine powder. 64.3278 g of the finely divided powder was recovered and was ready to be reduced.

Example: 90 wt % W-7 wt % Fe-3 wt % Ni

In the instant example, a 90 wt % W-7 wt % Fe-3 wt % Ni powder is synthesized that can yield ~50 g of a nano-particulate W—Fe—Ni metal powder. Standard grade AMT was used as the source of W, Nickel(II) Nitrate hexahydrate $(Ni(NO_3)_2.6H_2O$; F.W.=290.81 g/mole) was used as the source of Ni, and Iron(III) Nitrate nonahydrate $(Fe(NO_3)_3.9H_2O$; F.W.=404.00 g/mole) was used as the source of Fe. Ammonium Citrate (98%) (Am. Citrate; $(NH_4)_3C_6H_5O_7$; F.W.=243.22 g/mole), 70% Nitric Acid Solution, and deionized water were also included in the combustion synthesis solution.

Using the same methodology as described elsewhere herein, the molar ratio of the reactants required to produce a stoichiometric burn is as follows.

$$AMT:Fe(NO_3)_3:Ni(NO_3)_2:HNO_3:Am.\ Citrate=1:3.073:1.252:7.516:3.0$$

The amounts for preparing the combustion synthesis solution are as follows:
1) 62.1719 g of AMT (0.020397 mole of AMT)
2) ~100 g of D.I. water was used in this procedure 3) 25.3256 g (0.062687 mole) of $Fe(NO_3)_3 \cdot 9H_2O$
4) 7.4294 g (0.025547 mole) of $Ni(NO_3)_2 \cdot 6H_2O$
5) 3.0·(0.020397 mole)·243.22 g/mole of Ammonium Citrate÷0.98=15.1866 g of Ammonium Citrate
6) 7.516·(0.020397 mole)=0.153304 mole of $HNO_3$·63.01 g $HNO_3$ per mole·0.700=13.8000 g of 70% $HNO_3$ solution needed A 500 ml Erlenmeyer flask with a tight fitting screw cap was used for combustion synthesis solution preparation. The AMT was weighed out and transferred to the clean, dry Erlenmeyer flask. D.I. water was next added to the AMT solid in the flask. Then, the flask was capped and gently shaken periodically until all of the AMT solid had dissolved. The $Fe(NO_3)_3 \cdot 9H_2O$ was added to the solution in the flask and was dissolved without heat. The $Ni(NO_3)_2 \cdot 6H_2O$ was then added to the solution in the flask and also dissolved easily without heating. The Ammonium Citrate was dissolved in the solution in the flask. Finally, the 70% nitric acid solution was added to the contents of the flask. Initially, some precipitation occurs that redissolves upon further mixing of the solution. The combustion synthesis solution is then complete.

The combustion synthesis solution burn was carried out using a 4 L stainless steel beaker, which is heated on a hotplate to near red heat temperature. After the hotplate has heated the beaker bottom to near red heat, the entire combustion synthesis solution is quickly poured into the hot beaker, then the beaker was covered with a clean 100 mesh sieve to contain most of the solid particles produced, while allowing steam and combustion gasses to escape from the beaker. Steam is rapidly evolved for ~2-3 minutes, then red colored $NO_x$ fumes are evolved as the combustion process begins to initiate. When the $NO_x$ evolution subsides, the beaker containing the porous ash is removed from the hotplate and allowed to cool to room temperature. The entire burn process is typically completed within less than 10 minutes. After cooling, the ash is recovered from the beaker, and ground to a fine powder. 63.99 g of the finely divided powder was recovered and was ready to be reduced.

Example: Reduction of Combustion Product

As described elsewhere herein, after a combustion synthesis solution has been stoichiometrically burned, the resultant combustion product comprises a metal oxide. The metal oxide powder can then be reduced to yield a nanocrystalline metal powder according to embodiments of the present invention. In the present example, an agglomerate of an as-burnt oxide powder is ground using a mortar and pestle. The oxide powder is then loaded in a metal crucible (tungsten or molybdenum) with a metal cover and placed in a vacuum furnace or a tube furnace. After purging with nitrogen for ~30 min, hydrogen is supplied to the furnace. The oxide powder is reduced under hydrogen at the temperature in the range from 600° to 800° C. up to four hours in order to completely reduce the oxide powder to a nanocrystalline metal powder. To minimize the grain growth of the powder, fast heating and cooling (up to 100° C./min) is preferable. The resultant reduced powder forms moderately hard agglomerates of the metallic nanocrystallites, which can be broken down using a milling technique to achieve better densification.

Figure 2:
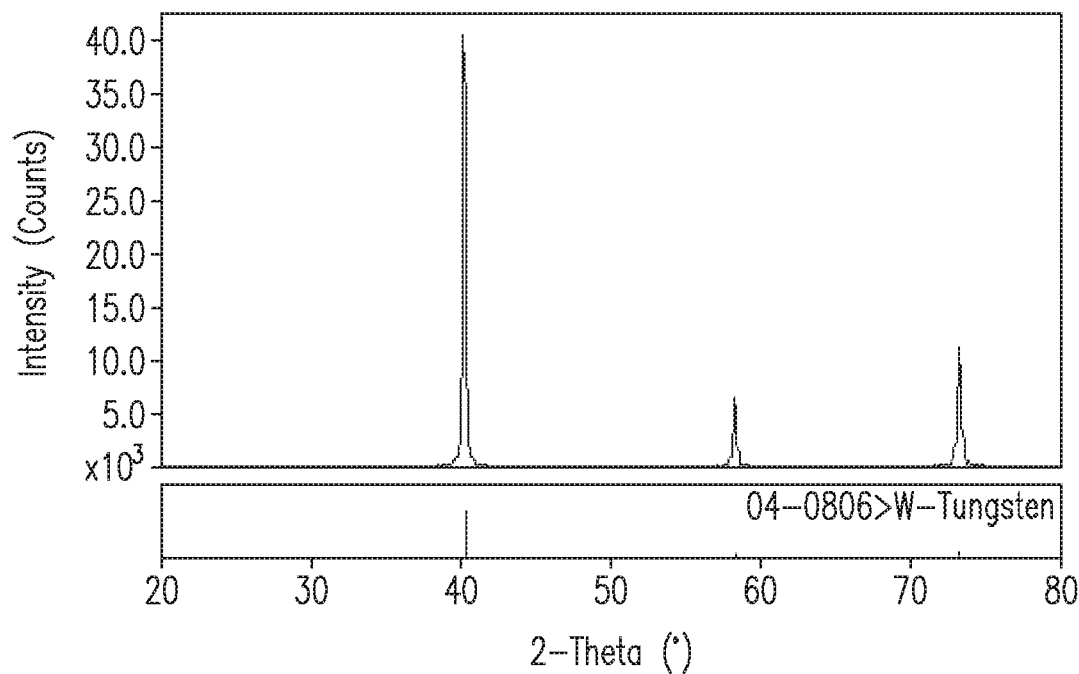
FIG. 2 is an X-ray diffraction pattern of a metallic tungsten powder after reduction of an oxide powder according to embodiments of the present invention.

Referring to FIG. 1, an X-ray diffraction (XRD) pattern is shown for a tungsten oxide powder prior to reduction. The XRD pattern indicates that the major phase is $WO_2$ and that the average grain size is 6.1 nm. Referring to FIG. 2, after reduction at 650° C. for approximately 4 hours, the oxide powder is reduced to metallic tungsten having an average grain size of 45.8 nm.

TABLE 1

Summary of crystallite size for various nanocrystalline metal and/or metal alloy powders synthesized according to embodiments of the present invention.

| Composition | Metal Salt(s) Used | Avg. Alloy Crystallite Size (nm) |
|---|---|---|
| 100W | AMT | 24.1 |
| 99.95W—0.05Ni | AMT, $Ni(NO_3)_2 \cdot 6H_2O$ | 28.3 |
| 99.5W—0.5Ni | AMT, $Ni(NO_3)_2 \cdot 6H_2O$ | 27.2 |
| 97W—3Ni | AMT, $Ni(NO_3)_2 \cdot 6H_2O$ | 28.3 |
| 99W—1$Y_2O_3$ | AMT, $Y(NO_3)_3 \cdot 6H_2O$ | 26.8 |
| 96W—4$Y_2O_3$ | AMT, $Y(NO_3)_3 \cdot 6H_2O$ | 27.6 |
| 95.5W—4$Y_2O_3$—0.5Ni | AMT, $Y(NO_3)_3 \cdot 6H_2O$, $Ni(NO_3)_2 \cdot 6H_2O$ | 30.0 |
| 96W—4Mo | AMT, $(NH_4)_6Mo_7O_{24} \cdot 4H_2O$ | 23.4 |
| 96W—4Re | AMT, $NH_4ReO_4$ | 26.9 |
| 94W—6Nb | AMT, $C_4H_4NNbO_9$ | 23.1 |
| 90W—7Fe—2Ni | AMT, $Fe(NO_3)_3 \cdot 9H_2O$, $Ni(NO_3)_2 \cdot 6H_2O$ | 31.5 |

Referring to Table 1, a summary of crystallite size is provided for a variety of nanocrystalline metal and/or metal alloy powders that were synthesized according to embodiments of the present invention.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. A method for synthesizing rhenium powders by a combustion reaction, the method comprising:
   forming a combustion synthesis solution by dissolving in water an oxidizer, a fuel, and at least one base-soluble, ammonium salt of rhenium in amounts that yield a stoichiometric burn when combusted; and
   heating the combustion synthesis solution to a temperature sufficient to substantially remove the water and to initiate a self-sustaining combustion reaction and form a rhenium oxide intermediate; and
   heating the rhenium oxide intermediate for less than 6 hours in a reducing atmosphere at a temperature lower than 850° C. to form the rhenium powders; and
   cooling the rhenium powders to a temperature below 100° C. and then introducing an oxidizing gas to passivate the surface of the rhenium powders.

2. The method of claim 1 further comprising dissolving a nitrate reagent of an alloying metal in the combustion synthesis solution.

3. The method of claim 1 wherein the oxidizer comprises a nitrate reagent.

4. The method of claim 1 wherein the oxidizer comprises nitric acid.

5. The method of claim 1 wherein the oxidizer comprises ammonium nitrate.

6. The method of claim 1 wherein the fuel comprises glycine.

7. The method of claim 1 wherein the fuel comprises a complexing agent.

8. The method of claim 1 wherein the base-soluble ammonium salt of rhenium is ammonium perrhenate.

\* \* \* \* \*

UNITED STATES PATENT AND TRADEMARK OFFICE
CERTIFICATE OF CORRECTION

PATENT NO. : 10,934,605 B2
APPLICATION NO. : 15/786289
DATED : October 17, 2017
INVENTOR(S) : John G. Fry et al.

Page 1 of 1

It is certified that error appears in the above-identified patent and that said Letters Patent is hereby corrected as shown below:

In the Specification

Column 4, Line 14 – Replace "$(NH_4)_6H_2W_{12}O_{40}.5H_2O$," with --$(NH_4)_6H_2W_{12}O_{40} \cdot 5H_2O$,--

Column 6, Line 12 – Replace "$(O)(C_2O_4)_2.xH_2O$;" with --$(O)(C_2O_4)_2 \cdot xH_2O$;--

Column 8, Line 51 – Replace "$(Ni(NO_3)_2.6H_2O$;" with --$(Ni(NO_3)_2 \cdot 6H_2O$;--

Column 8, Line 53 – Replace "$(Fe(NO_3)_3.9H_2O$;" with --$(Fe(NO_3)_3 \cdot 9H_2O$;--

Column 9, Line 1 – Replace "$Fe(NO_3)_3.9H_2O$" with --$Fe(NO_3)_3 \cdot 9H_2O$--

Column 9, Line 2 – Replace "$Ni(NO_3)_2.6H_2O$" with --$Ni(NO_3)_2 \cdot 6H_2O$--

Column 9, Line 14 – Replace "$Fe(NO_3)_3.9H_2O$" with --$Fe(NO_3)_3 \cdot 9H_2O$--

Column 9, Line 15 – Replace "$Ni(NO_3)_2.6H_2O$" with --$Ni(NO_3)_2 \cdot 6H_2O$--

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*